Jan. 26, 1954 F. W. ANDERSON Plant Pat. 1,247
PEACH TREE
Filed March 17, 1953
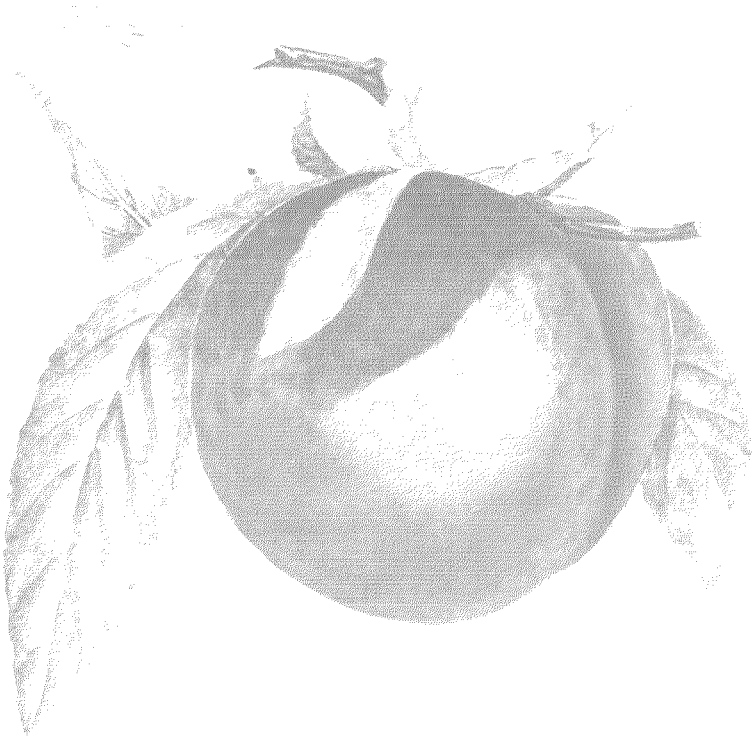
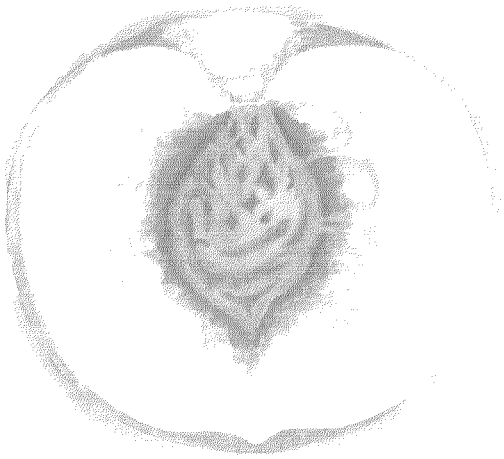
WITNESS
Addison H. Avery
INVENTOR
Frederic W. Anderson
Walter Norris
ATTYS.

Patented Jan. 26, 1954

Plant Pat. 1,247

UNITED STATES PATENT OFFICE 1,247

PEACH TREE

Frederic W. Anderson, Merced, Calif.

Application March 17, 1953, Serial No. 343,005

1 Claim. (Cl. 47—62)

This invention relates to a new and distinct variety of peach tree characterized by self-fertile flowers, and by large, highly colored, freestone fruit of excellent eating quality, which recommends it highly for market and dessert use.

This variety is a cross of the Le Grand nectarine (United States Plant Patent 549) and the Elberta peach (unpatented); the variety having been originated and asexually reproduced by me in my experimental nursery and orchard near Le Grand, county of Merced, California, in the following manner:

All of the flowers of a number of Le Grand nectarine trees were emasculated and pollen from Elberta peach flowers was applied to the pistils. The resulting seeds were gathered and planted, and from which seeds grew a number of seedlings.

When such seedlings were of a sufficient size, bud wood was taken and top-worked onto mature root stock; all of such top-workings being yellow fleshed peaches, and one was conspicuous because of its unusual size, and high color, somewhat resembling the J. H. Hale peach (unpatented) in these particulars.

Further observation and examination disclosed that such one variety, in addition to the characteristics enumerated, had the other desirable qualities required of a commercial peach, whereupon a substantial number of the variety were further top-worked on mature root stock for additional observation and testing. Such later asexual reproductions bore all of the desirable characteristics of the original tree and the initial top-workings.

At the same time that the later top-workings were undertaken I also top-worked on the same root stock bud wood of the J. H. Hale peach in order that an accurate comparison could be made. When the top-workings of the present variety and the J. H. Hale peach bore fruit, observations and comparisons of the same were made, as follows:

As compared to the J. H. Hale peach the present variety exhibited more red outside color and was ready for harvest about three or four days earlier. The fruit of the two varieties under comparison averaged the same weight; i. e. about one-half pound each, although a few left on each tree reached approximately a pound in weight. Both varieties are almost globose in shape, although occasional specimens of the instant variety are slightly elongated axially. The average diameter of the two varieties is approximately three inches in both planes, although specimens of both reached four inches.

The present variety showed and retained much more color during all stages of the ripening period, which was approximately two weeks for both varieties, and both cling to the tree remarkably well during such ripening period.

The present variety has flowers with red anthers, and is self-fertile, while the J. H. Hale peach has yellow anthers in common with other self-sterile peach varieties.

As further distinguished from the J. H. Hale peach, the fruit of the present variety has less acidity, and is of a much better eating quality.

Still further distinctive characteristics of the present variety is that the tree is larger, more vigorous and more productive than the J. H. Hale peach tree.

In the original drawings:

Fig. 1 is an elevation of one of the fruit, together with twigs and leaves.

Fig. 2 is a sectional elevation of one of the fruit, with the stone exposed.

Referring now more specifically to the pomological details of this new and distinct variety of peach tree, the following is an outline description thereof; all major color plate identifications being by reference to Maerz and Paul Dictionary of Color:

Tree: Large; vigorous; spreading; open; vase formed; productive; regular bearer.

Trunk: Medium size; medium texture.

Branches: Medium size; medium texture.

*Color.*—Brown.

*Lenticels.*—Medium number; medium size.

Leaves: Large. Average length—6¾ inches. Average width—1½ inches. Medium thickness.

*Color.*—Top side—medium green (22–L–7). Under side—lighter green (22–H–4).

*Margin.*—Glandular; crenate.

*Petiole.*—Medium length; medium thickness.

*Glands.*—Average number—four. Opposite; medium; reniform. Position—usually two on petiole and two to four on blade.

Flower buds: Large size; medium length.

Flowers:

*Dates first and full bloom.*—Average—two to three days before Elberta peach (unpatented). Medium early.

*Size.*—Large like Fay Elberta peach (unpatented).

Fruit: Maturity when described—Hard ripe, August 5, 1952. Dates of first and last pickings—July 25–August 10, 1952.

*Size.*—Uniform; large. Average diameter axially—three to four inches. Transverse in suture plane—three to four inches. Largest specimens weigh up to a pound; same size class as J. H. Hale peach.

*Form.*—Uniform; symmetrical; globose to slightly oblong.

*Suture.*—An inconspicuous line; shallow; has slight depression beyond pistil point.

*Ventral surface.*—Rounded strongly; lips equal.

*Cavity.* — Rounded. Depth — ½ inch. Breadth—1½ inch. Markings smooth.

*Base.*—Rounded.

*Apex.*—Short.

Skin: Medium thick; medium texture.

*Tendency to crack.*—None.

*Down.*—Short.

*Color.*—Yellow (10–J–7, shading to 11–K–9), with substantial overspreading of red (4–K–10), mottled with darker red (7–L–1).

Flesh:

*Color.*—Yellow (9–L–6 shading to 9–L–7) with substantial red (4–L–6) at stone, streaking out lighter red (4–L–7).

*Amygdalin.*—Moderate.

*Juice.*—Abundant.

*Texture.*—Firm; meaty; melting.

*Fibers.*—Abundant.

*Ripens.*—Evenly.

*Flavor.*—Delicate.

*Aroma.*—Distinct.

*Eating quality.*— Best; lacks acidity of J. H. Hale (unpatented) and Rio Oso, Gem (United States Plant Patent 84).

Stone: Free. Fibres—long; retains short fibre-like threads along ridges toward base.

*Size.*—Medium. Average length—1⅝ inches. Average breadth—1¼ inch. Average thickness—¾ inch.

*Form.*—Oval.

*Base.*—Straight to oblique.

*Hilum.*—Narrow.

*Apex.*—Acute.

*Surface.*—Irregularly furrowed near base; ridged throughout; pitted throughout.

*Ridges.*—Jagged toward apex.

*Ventral edge.*—Thick with wing toward base.

*Dorsal edge.*—Full, with broad groove toward base.

*Ridges.*—Interrupted.

*Sides.*—Equal.

*Tendency to split.*—Slight.

*Color.*—Brown (7–H–12).

Keeping quality: Good.

Use: Market; dessert.

Shipping quality: Good.

The tree and its fruit herein described may vary in slight detail due to climatic and soil conditions under which the variety may be grown.

Having thus described my invention, I claim:

A new and distinct variety of peach tree, as described and illustrated, bearing large size, firm, meaty and melting, yellow fleshed freestone fruit having yellow skin with substantial overspreading of red; characterized—in comparison with the J. H. Hale peach—by a ripening period three to four days earlier; of substantially the same size but more red exterior color; self-fertile instead of self-sterile flowers; having red instead of yellow anthers; and less acidity with better eating quality; and further characterized by a tree which is larger, more vigorous, and more productive than the J. H. Hale peach tree.

FREDERIC W. ANDERSON.

No references cited.